(12) United States Patent
Munn

(10) Patent No.: US 11,037,086 B2
(45) Date of Patent: Jun. 15, 2021

(54) METHOD AND SYSTEM FOR EVALUATING THE PERFORMANCE OF A READER OF SCREENING MAMMOGRAMS

(71) Applicant: Charles Samson Munn, Rancho Palos Verdes, CA (US)

(72) Inventor: Charles Samson Munn, Rancho Palos Verdes, CA (US)

( * ) Notice: Subject to any disclaimer, the term of this patent is extended or adjusted under 35 U.S.C. 154(b) by 317 days.

(21) Appl. No.: 15/997,142

(22) Filed: Jun. 4, 2018

(65) Prior Publication Data

US 2019/0370723 A1    Dec. 5, 2019

(51) Int. Cl.
*G06Q 10/06* (2012.01)
*G16H 30/20* (2018.01)
*G16H 40/20* (2018.01)

(52) U.S. Cl.
CPC ....... *G06Q 10/06398* (2013.01); *G16H 30/20* (2018.01); *G16H 40/20* (2018.01)

(58) Field of Classification Search
CPC .......................... G09Q 10/06398; G09B 23/28
See application file for complete search history.

(56) References Cited

U.S. PATENT DOCUMENTS

| 5,797,130 A | * | 8/1998 | Nelson | ............... | G01N 15/1468 |
| | | | | | 705/7.42 |
| 2015/0079566 A1 | * | 3/2015 | Salkowski | ........... | G09B 23/286 |
| | | | | | 434/262 |

OTHER PUBLICATIONS

Tan et al., "Comparison of readers' detection of right-sided and left-sided breast cancers and microcalcifications," Journal of Medical Imaging and Radiation Oncology, 55:353-361 (2011).
Soh et al., "Assessing reader performance in radiology, an imperfect science: Lessons from breast screening," Clinical Radiology, 67: 623-628 (2012).
Rauscher et al., "Beyond MQSA: Measuring the quality of breast cancer screening programs," Am J Roentgenol., 202(1): 145-151 (2014).
Feig, "Auditing and Benchmarks in Screening and Diagnostic Mammography," Radiol Clin N Am, 45:791-800 (2007).
MRS7 Mammography Reporting System Statistical Reports Supplement, Mammography Reporting System Inc., Lynnwood, Washington (2016).

(Continued)

*Primary Examiner* — James S. McClellan
(74) *Attorney, Agent, or Firm* — Kriegsman & Kriegsman

(57) ABSTRACT

Method and system for evaluating the performance of a reader of screening mammograms. According to one embodiment, the system includes a performance evaluator that is in electronic communication with both one or more readers of screening mammograms and one or more supervisors. The performance evaluator is configured to collect information from each reader as to whether a recall request is a bilateral or unilateral recall request and, if a unilateral recall request, is for a left breast or right breast. In addition, the performance evaluator is designed to use such information to assess the performance of one or more readers by comparing the observed bilateral recall request rate to a standard bilateral recall request rate and/or by comparing the numbers of left breast recall requests and right breast recall requests to expected numbers of the same. The performance assessment is then available for electronic retrieval by any authorized supervisor.

21 Claims, 7 Drawing Sheets

(56) References Cited

OTHER PUBLICATIONS

Understanding MagView QA Reports: MagView Help Center, MagView, Burtonsville, Maryland (published prior to the filing of the present application).
MagView Quality Assurance Summary Report, MagView, Burtonsville, Maryland (Jan. 13, 2018).
PenTips #179: Restrictive Recalls, PenRad Technologies, Inc., Buffalo, Minnesota (2017).
PenRad Administrative Reports Handbook, PenRad Technologies, Inc., Buffalo, Minnesota (2015).

* cited by examiner

| Reader | Total Unilateral Call-Back Requests | Left Breast Call-Back Request | Right Breast Call-Back Requests | Statistical Conclusion |
|---|---|---|---|---|
| 15-1 | 60 | 32 (53.3%) | 28 (46.7%) | Acceptable Performance |
| 15-2 | 75 | 50 (66.7%) | 25 (33.3%) | Unacceptable Performance – left/right ratio too high |
| 15-n | 4 | 3 (75.0%) | 1 (25.0%) | Acceptable Performance |

Fig. 4

| Reader | Total Screenings | Bilateral Call-Back Requests | Conclusion |
|---|---|---|---|
| 15-1 | 728 | 44 (6.0%) | Acceptable Performance |
| 15-2 | 911 | 1 (0.1%) | Unacceptable Performance – bilateral rate too low |
| 15-n | 25 | 2 (8.0%) | Acceptable Performance |

Fig. 5

METHOD AND SYSTEM FOR EVALUATING THE PERFORMANCE OF A READER OF SCREENING MAMMOGRAMS

BACKGROUND OF THE INVENTION

The present invention relates generally to the field of mammography and relates more particularly to techniques for evaluating the performance of readers of screening mammograms.

Mammography is a well-known technique that uses x-rays to generate an image of a breast. The examination of the breast thus generated is typically referred to as a mammogram. In many cases, a mammogram is composed of two-dimensional images; however, some newer mammography techniques utilize a plurality of two-dimensional image data taken at different angles of a breast to generate three-dimensional images and/or a series of images which (when taken together) compose the three-dimensional volume of the breast.

A screening mammogram is a test in which one or more mammogram views (typically two two-dimensional images obtained at different angles) are obtained for each breast of a patient who shows no prior signs or symptoms of breast cancer. The images obtained in a screening mammogram are then typically viewed (in "reading" or interpreting) by medical personnel (herein, "a reader"), typically a radiologist, to determine if there are any image findings or abnormalities in the images. Such findings or abnormalities may include, for example, the appearance of objects that are probative of breast cancer, such as masses or clusters of microcalcifications, or the appearance of other indeterminate features. If, based on the reading of the images of the screening mammogram, the reader believes that further investigation is warranted, the reader typically issues or otherwise initiates a recall request, recommendation, or advisory (sometimes referred to herein synonymously as a recall request or a call-back request), i.e., a communication to the patient and/or to the patient's health-care provider, requesting that the patient come back soon (i.e., as soon as is convenient, typically within six weeks in the U.S., currently) for a recall or call-back (i.e., further testing). The recall request (or call-back request) may be for a patient with regard to one breast (a unilateral recall request (or unilateral call-back request) of either the left or right breast) or may be for a patient with regard to both breasts (a bilateral recall request (or bilateral call-back request)). Such further testing could include, for example, a diagnostic mammogram, an ultrasound, a biopsy, magnetic resonance imaging, or some combination thereof, unilateral or bilateral. To be clear, recall and call-back are terms applied as a matter of art and herein distinct from follow-up testing, which does not occur so soon, but rather occurs explicitly months later, typically three to twelve months later and commonly four to six months later.

Generally speaking, as part of reading the images of a screening mammogram, the reader prepares a report (also known as an interpretation) in which the results of the screening mammogram are presented and an indication of any needed future action, such as a recall, is provided. Although such a report may be embodied in paper form, it has become increasingly more common for such reports to be created and stored in electronic form. Examples of software that are currently commercially available for the creation and storage of such reports include PENRAD™ software (PenRad Technologies, Inc., Buffalo, Minn.), MAGVIEW® software (Applied Software, Inc., Burtonsville, Md.), and MRS™ software (Mammography Reporting System, Inc., Lynnwood, Wash.).

As can readily be appreciated, the reading of images of a screening mammogram to detect abnormalities and to determine whether or not a recall is warranted requires considerable skill and judgment by the reader. Such skill and judgment may vary significantly from reader to reader, ultimately reflected in variation in quality of readers' reports, including requests for recall. As a result, in order to improve quality of readers' reports, including to decrease unwarranted recalls as well as to increase merited recalls, it would be desirable to be able to assess the performance of a screening mammogram reader or a particular group of readers. One way to assess such performance is to have a second reader, such as a supervisor, review the results of an initial reader (or group of readers) and determine whether or not the findings of the initial reader should be confirmed. However, such an approach is labor-intensive, time-consuming, and costly, particularly where the second reader is entrusted with reviewing the results of a plurality of initial readers. Moreover, such an approach presupposes that the readings of the second reader are, themselves, objectively correct or ideal, so that all deviations from the readings of the second reader can be regarded as errors. Unfortunately, however, such a presupposition is, itself, flawed as it cannot be assumed that the second reader will correctly or ideally read every screening mammogram.

Another way to assess the performance of a screening mammogram reader is to compare one or more metrics of the reader or of the particular group of readers in reading a plurality of screening mammograms to established or expected norms for such a plurality of screening mammograms. In this manner, significant deviations with respect to such one or more metrics for the plurality of screening mammograms can be used to signal a departure from acceptable performance. At present, there are many such metrics. Examples of such metrics include recall rate (i.e., the proportion of total screenings read by a reader in which the reader issues a recall request or call-back request), cancer detection rate (i.e., the number of breast cancers detected following an abnormal screen for every 1000 screening mammograms performed), and early cancer detection rate (i.e., the proportion of screen-detected breast cancers that were either in situ or stage 1). Additional information regarding performance metrics for assessing readers of screening mammograms may be found in the following documents, all of which are incorporated herein by reference: Feig, "Auditing and Benchmarks in Screening and Diagnostic Mammography," *Radiol Clin N Am*, 45:791-800 (2007); Soh et al., "Assessing reader performance in radiology, an imperfect science: Lessons from breast screening," *Clinical Radiology*, 67:623-628 (2012); and Rauscher et al., "Beyond MQSA: Measuring the quality of breast cancer screening programs," *Am J Roentgenol*, 202(1):145-151 (2014).

Moreover, some commercially available software programs used in creating and storing screening mammography reports also include capabilities for quantifying certain metrics, such as recall rate. (See, for example, PenRad Mammography Administrative Reports Handbook, ©1995-2015, PenRad Technologies, Inc., Buffalo, Minn.; and MRS7 Mammography Reporting System Statistical Reports Supplement, Mammography Reporting System Inc., Lynnwood, Wash., both of which are incorporated herein by reference.)

Although existing metrics are useful in assessing the performance of screening mammogram readers, such metrics do not account for all possible performance variations that may occur. As a result, there is a need to identify additional metrics that may be used to assess the performance of screening mammogram readers, such as those that may evaluate elements of such performance not assessed or not assessed sufficiently, directly or indirectly, by current metrics.

SUMMARY OF THE INVENTION

It is an object of the present invention to provide a new method and system for evaluating the performance of a screening mammogram reader.

According to one aspect of the invention, there is provided a system for evaluating the performance of at least one screening mammogram reader, the system comprising: (a) a performance evaluator, the performance evaluator comprising a central controller; and (b) a first compute device, the first compute device being adapted for use by a first screening mammogram reader, the first compute device being in electronic communication with the central controller, wherein call-back request information associated with the first screening mammogram reader is uploaded from the first compute device to the central controller and wherein the call-back request information comprises an indication as to whether a unilateral call-back request is for a left breast or for a right breast; (c) wherein the performance evaluator aggregates the call-back request information for unilateral call-back requests uploaded from the first compute device and wherein the central controller for the performance evaluator makes an assessment of lateral bias (i.e., left call-back requests versus right call-back requests) for unilateral call-back requests of the first screening mammogram reader based on the aggregated unilateral call-back request information.

In a more detailed feature of the invention, the aggregated unilateral call-back request information may comprise an observed number of left breast call-back requests and an observed number of right breast call-back requests for the first screening mammogram reader, and the central controller may assess lateral bias by comparing the observed numbers of left breast call-back requests and right breast call-back requests for the first screening mammogram reader to expected numbers of left breast call-back requests and right breast call-back requests, respectively.

In a more detailed feature of the invention, the central controller may compare the observed numbers of left and right breast call-back requests for the first screening mammogram reader to expected numbers of left and right breast call-back requests, respectively, using a chi-square, other statistical evaluation and/or simple arithmetic comparison.

In a more detailed feature of the invention, the first compute device may be selected from the group consisting of one or more of a desktop computer, a laptop computer, a smartphone, and a kiosk-type workstation, whether used alternatively or in combination.

In a more detailed feature of the invention, the system may further comprise a second compute device, the second compute device may be adapted for use by a first supervising entity, and the second compute device may be in electronic communication with the central controller.

In a more detailed feature of the invention, the second compute device may be selected from the group consisting of one or more of a desktop computer, a laptop computer, a smartphone, and a kiosk-type workstation, whether used alternatively or in combination.

In a more detailed feature of the invention, the assessment of lateral bias for the first screening mammogram reader may be retrievable by the first supervising entity using the second compute device.

In a more detailed feature of the invention, the performance evaluator may automatically send a notification to the second compute device when the central controller determines a presence of lateral bias.

In a more detailed feature of the invention, the system may further comprise a third compute device, the third compute device may be adapted for use by a second screening mammogram reader, the third compute device may be in electronic communication with the central controller, call-back request information associated with the second screening mammogram reader may be uploaded from the third compute device to the central controller, the call-back request information associated with the second screening mammogram reader may comprise an indication as to whether a unilateral call-back request is for a left breast or for a right breast, the performance evaluator may aggregate the call-back request information for unilateral call-back requests uploaded from the third compute device, and the central controller for the performance evaluator may issue an assessment of lateral bias regarding unilateral call-back requests of the second screening mammogram reader based on the aggregated unilateral call-back request information.

In a more detailed feature of the invention, the assessment of lateral bias for the second screening mammogram reader may be retrievable by the first supervising entity using the second compute device.

In a more detailed feature of the invention, at least one of the performance evaluator and the first compute device may be integrated with at least one of voice-recognition software and/or hardware; an electronic medical record apparatus; mammography reporting and analysis software; and radiology reporting software and/or hardware.

According to another aspect of the invention, there is provided a system for evaluating the performance of at least one screening mammogram reader, the system comprising: (a) a performance evaluator, the performance evaluator comprising a central controller; and (b) a first compute device, the first compute device being adapted for use by a first screening mammogram reader, the first compute device being in electronic communication with the central controller, wherein call-back request information associated with the first screening mammogram reader is uploaded from the first compute device to the central controller and wherein the call-back request information comprises an indication as to whether or not the first screening mammogram reader is advising a bilateral call-back request; (c) wherein the performance evaluator aggregates the call-back request information for bilateral call-back requests uploaded from the first compute device and wherein the central controller for the performance evaluator makes an assessment of bilateral bias (i.e., too many or too few bilateral call-back requests) of the first screening mammogram reader based on the aggregated bilateral call-back request information.

In a more detailed feature of the invention, the aggregated bilateral call-back information may comprise an observed number of bilateral call-back requests and an observed number of other outcomes for the first screening mammogram reader, and the central controller may assess bilateral bias by comparing the observed numbers of bilateral call-back requests and other outcomes for the first screening mammogram reader to expected numbers of bilateral call-back requests and other outcomes, respectively.

In a more detailed feature of the invention, the central controller may compare the observed numbers of bilateral call-back requests and other outcomes for the first screening mammogram reader to expected numbers of bilateral call-back requests and other outcomes, respectively, using a chi-square, other statistical evaluation and/or simple arithmetic comparison.

In a more detailed feature of the invention, the first compute device may be selected from the group consisting of one or more of a desktop computer, a laptop computer, a smartphone, and a kiosk-type workstation, whether used alternatively or in combination.

In a more detailed feature of the invention, the system may further comprise a second compute device, the second compute device may be adapted for use by a supervising entity, and the second compute device may be in electronic communication with the central controller.

In a more detailed feature of the invention, the second compute device may be selected from the group consisting of one or more of a desktop computer, a laptop computer, a smartphone, and a kiosk-type workstation, whether used alternatively or in combination.

In a more detailed feature of the invention, the assessment of bilateral bias by the first screening mammogram reader may be retrievable by the supervising entity using the second compute device.

In a more detailed feature of the invention, the system may further comprise a third compute device, the third compute device may be adapted for use by a second screening mammogram reader, the third compute device may be in electronic communication with the central controller, call-back request information associated with the second screening mammogram reader may be uploaded from the third compute device to the central controller, the call-back request information associated with the second screening mammogram reader may comprise an indication as to whether or not the second screening mammogram reader is advising a bilateral call-back request, the performance evaluator may aggregate the call-back request information uploaded from the third compute device, and the central controller for the performance evaluator may make an assessment of bilateral bias for the second screening mammogram reader based on the aggregated bilateral call-back request information.

In a more detailed feature of the invention, the assessment of bilateral bias for the second screening mammogram reader may be retrievable by the first supervising entity using the second compute device.

In a more detailed feature of the invention, at least one of the performance evaluator and the first compute device may be integrated with at least one of voice-recognition software and/or hardware; an electronic medical record apparatus; mammography reporting and analysis software; and radiology reporting software and/or hardware.

According to yet another aspect of the invention, there is provided a system for evaluating the performance of at least one screening mammogram reader, the system comprising: (a) a performance evaluator, the performance evaluator comprising a central controller; and (b) a first compute device, the first compute device being adapted for use by a first screening mammogram reader, the first compute device being in electronic communication with the central controller, wherein call-back request information associated with the first screening mammogram reader is uploaded from the first compute device to the central controller and wherein the call-back request information comprises an indication that a call-back request is being advised for a left breast, a right breast, both breasts, or neither breast; (c) wherein the performance evaluator aggregates the call-back request information uploaded from the first compute device and wherein the central controller for the performance evaluator, based on the aggregated call-back request information, assesses the first screening mammogram reader for lateral bias regarding unilateral call-back requests and/or assesses the first screening mammogram reader for bilateral bias.

In a more detailed feature of the invention, at least one of the performance evaluator and the first compute device may be integrated with at least one of voice-recognition software and/or hardware; an electronic medical record apparatus; mammography reporting and analysis software; and radiology reporting software and/or hardware.

According to still another aspect of the invention, there is provided a method for evaluating the performance of at least one screening mammogram reader, the method comprising the steps of: (a) providing a performance evaluator, the performance evaluator comprising a central controller; (b) uploading call-back request information associated with a first screening mammogram reader onto the central controller using a first compute device in electronic communication therewith, the call-back request information comprising an indication as to whether a unilateral call-back request is for a left breast or for a right breast; (c) aggregating, using the performance evaluator, the call-back request information for unilateral call-back requests uploaded from the first compute device, and (d) using the central controller for the performance evaluator to make an assessment of lateral bias for unilateral call-back requests of the first screening mammogram reader based on the aggregated unilateral call-back request information.

According to still yet another aspect of the invention, there is provided a method for evaluating the performance of at least one screening mammogram reader, the method comprising the steps of: (a) providing a performance evaluator, the performance evaluator comprising a central controller; (b) uploading call-back request information associated with a first screening mammogram reader onto the central controller using a first compute device in electronic communication therewith, the call-back request information comprising an indication as to whether or not the first screening mammogram reader is advising a bilateral call-back request; (c) aggregating, using the performance evaluator, the call-back request information for bilateral call-back requests uploaded from the first compute device, and (d) using the central controller for the performance evaluator to make an assessment of bilateral bias for the first screening mammogram reader based on the aggregated bilateral call-back request information.

According to a further aspect of the invention, there is provided a method for evaluating the performance of at least one screening mammogram reader, the method comprising the steps of: (a) providing a performance evaluator, the performance evaluator comprising a central controller; (b) uploading call-back request information associated with a first screening mammogram reader onto the central controller using a first compute device in electronic communication therewith, the call-back request information comprising an indication as to whether the first screening mammogram reader is advising a call-back request for a left breast, a right breast, both breasts, or neither breast; (c) aggregating, using the performance evaluator, the call-back request information uploaded from the first compute device, and (d) using the central controller for the performance evaluator to make an assessment of the first screening mammogram reader regarding lateral bias in unilateral call-back requests and/or regarding bilateral bias in bilateral call-back requests.

Additional objects, as well as aspects, features and advantages, of the present invention will be set forth in part in the description which follows, and in part will be obvious from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. These drawings are not necessarily drawn to scale, and certain components may have undersized and/or oversized dimensions for purposes of explication. In the drawings wherein like reference numeral represent like parts:

FIG. 4 is a sample unilateral call-back request table stored by the performance evaluator shown in FIG. 1, the sample unilateral call-back request table being useful in understanding the process by which the performance evaluator may analyze unilateral call-back request information to evaluate performance of one or more screening mammogram readers;

FIG. 5 is a sample bilateral call-back request table stored by the performance evaluator shown in FIG. 1, the sample bilateral call-back request table being useful in understanding the process by which the performance evaluator may analyze bilateral call-back request information to evaluate performance of one or more screening mammogram readers;

DETAILED DESCRIPTION OF THE INVENTION

Figure 1:
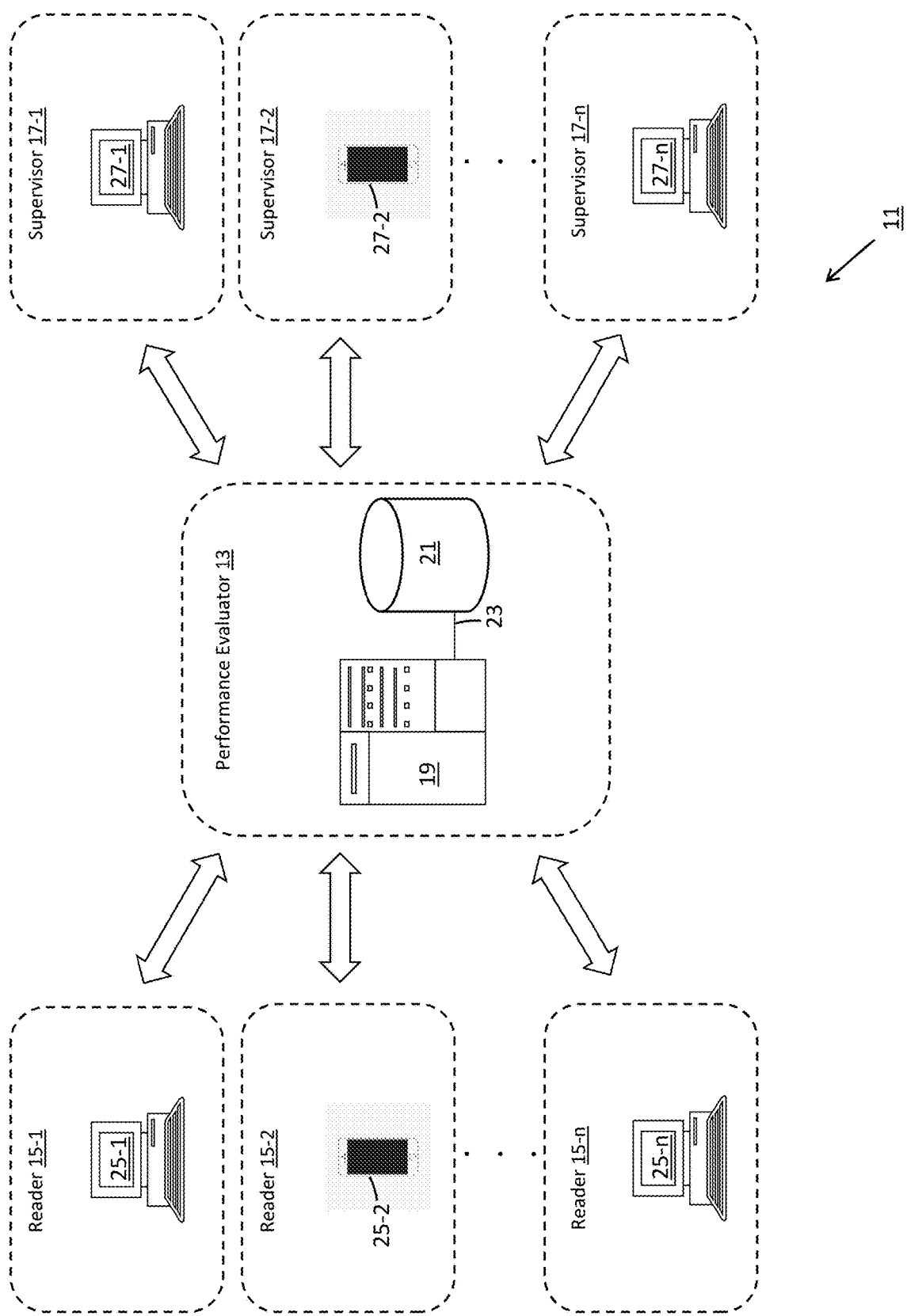
FIG. 1 is a simplified schematic representation of one embodiment of a system for evaluating the performance of a screening mammogram reader, the system being constructed according to the teachings of the present invention.

The present invention is based, at least in part, on the discovery of new metrics that may be used to assess the performance of a reader (or of a particular group of readers) of screening mammograms. In particular, the present inventor has discovered that one such metric for assessing the performance of a screening mammogram reader is the relative number of left breast recall requests to right breast recall requests among all unilateral recall requests issued by the reader. In addition, another metric discovered by the present inventor for assessing the performance of a screening mammogram reader is the reader's bilateral recall request rate. For purposes of the present specification and claims, the term "bilateral recall request rate" may be alternatively defined as (1) the proportion of total screenings read by a reader (or by a plurality of readers) in which the reader (or plurality of readers) requests that the patient come back for further testing of both the left breast and the right breast or (2) the proportion of total call-back requests issued by a reader (or by a plurality of readers) in which the reader (or plurality of readers) requests that a patient come back for further testing of both the left breast and the right breast.

To date, and despite extensive research and voluminous publications regarding mammography, information about the rate at which a screening mammogram reader (or a particular group of readers) issues recall requests to patients for diagnostic testing of left breasts as compared to the rate at which the same reader (or group of readers) issues recall requests to patients for diagnostic testing of right breasts, and/or information about the rate at which a screening mammogram reader (or a particular group of readers) issues recall requests to patients for diagnostic testing of both breasts has received no attention—not even mention—as possible performance or quality metrics. (As noted above, the diagnostic testing at the call-back (or recall) may involve, for example, a diagnostic mammogram, an ultrasound, a biopsy, magnetic resonance imaging, or some combination thereof.)

In fact, although existing automated systems used in the creation, storage, and/or analysis of screening mammogram reports may incidentally record in individual patients' reports that a request is being made that a patient be recalled for a left breast and/or that a request is being made that a patient be recalled for a right breast, such systems are not configured to collect nor even to store this type of information in a way as to enable a determination, in an automated fashion, of rates at which patients are being issued recall requests for a left breast, a right breast, or both breasts, such as rates specific to an individual reader (or to a particular group of readers), or to a specified period of time, let alone the capability of using this information to assess the performance of a reader (or a particular group of readers), or the performance during a specified period of time.

By contrast, the present invention is directed, at least in part, at an automated system that is designed to collect information as to whether a recall request is a bilateral recall request or a unilateral recall request and, if a unilateral recall request, is a left breast recall request or a right breast recall request. Moreover, the automated system of the present invention is designed to use such information to assess the performance of the reader (or a group of readers), for example, by comparing a reader's (or a group of readers') bilateral recall request rate to standard bilateral recall request rates and/or by comparing a reader's (or a group of readers') relative numbers of left breast recall requests and right breast recall requests to expected relative numbers of left breast recall requests and right breast recall requests for the same number of unilateral recall requests.

Reader Performance Evaluation System 11

Referring now to FIG. 1, there is shown a simplified schematic representation of one embodiment of a system for evaluating the performance of at least one reader of screening mammograms, the system being constructed according to the teachings of the present invention and identified generally by reference numeral 11. As will be described in detail below, system 11 preferably is configured to aggregate and to analyze historical call-back request data in order to evaluate the performance of a screening mammogram reader or a particular group of such readers.

As can be seen, evaluation system 11 comprises a performance evaluator 13 that is in electronic communication with both a plurality of individual screening mammogram readers 15-1 through 15-$n$ and a plurality of supervising entities, or supervisors, 17-1 through 17-$n$. Screening mammogram readers 15-1 through 15-$n$ are typically radiologists but, alternatively, may be any healthcare provider authorized to read a screening mammogram. Supervisors 17-1 through 17-$n$ may be one or more of medical supervisors, hospital administrators, health insurance overseers, or other individuals in the healthcare industry or elsewhere with oversight authority. As a principal feature of the present invention, performance evaluator 13 aggregates call-back request information from each of the plurality of readers 15. In turn, performance evaluator 13 analyzes the call-back request information for one or more readers 15, based on one or more metrics and using one or more statistical algorithms, in order to generate an assessment of the one or more readers 15 in reading screening mammograms. The performance assessment and associated metrics for the one or more readers 15 are then available for electronic retrieval by any supervisor 17 that is properly authorized and verified by evaluator 13 to review the performance of the particular one or more readers 15.

Performance evaluator 13 preferably includes a central controller 19 and a data storage device 21 in electronic communication with one another via a network path 23. It is to be understood that central controller 19 and data storage device 21 may be housed at a common facility or may be remotely connected (e.g., as part of a cloud-based data storage solution). It is also to be understood that central controller 19 and/or data storage device 21 may be housed and/or function within (or be incorporated into) devices used for voice-recognition reporting, for an electronic medical record, for mammography reporting, for general radiology reporting, etc. It is also to be understood that performance evaluator 13 may be located at a common facility with one or more readers 15 and one or more supervisors 17 (i.e., as part of a closed network, such as a hospital) or, in the alternative, may be remotely located at a standalone facility (e.g., as part of an open network for use by multiple, otherwise unrelated, healthcare-related entities). In any of the above environments, performance evaluator 13 is preferably suitably designed to ensure sensitive data are only available for inspection by properly authorized parties.

As can be appreciated, central controller 19 serves as the central functional hub of system 11. In the present embodiment, central controller 19 is shown as a web server that readily allows for the exchange of data through one or more designated web pages. However, it is to be understood that central controller 19 could be in the form of (or housed or integrated into) any host computer that is programmed to communicate with other compute devices through a designated network (e.g., an intranet).

Data storage device, or database, 21 represents any device that is designed to store information associated with the screening mammograms and related performance assessments for each of readers 15. As will be explained further below, the data for multiple related readers 15 (e.g., readers 15 reading at a common institution, at the same or at different campuses/sites/offices) may be grouped or otherwise linked together to facilitate retrieval by a corresponding one or more supervisors 17. In this manner, a single supervisor 17 or multiple supervisors 17 may review the performance of one or more readers 15, either individually or as part of a collective group.

As referenced above, a plurality of readers 15-1 through 15-$n$ is maintained in electronic communication with performance evaluator 13. Preferably, system 11 is appropriately scaled to support any number of concurrent users (e.g., readers 15 or supervisors 17) without departing from the spirit of the present invention.

As noted above, each reader 15 represents a medical professional who reads screening mammograms. In most cases, readers 15 will be radiologists but need not necessarily be. Readers 15-1 through 15-$n$ are represented herein as being independently linked with central controller 19 using corresponding compute devices 25-1 through 25-$n$, respectively.

Compute device 25 represents any type of compute device that is adapted to interface with central controller 19 (e.g., through a designated web page or mobile application). Solely for purposes of example, compute devices 25-1 and 25-$n$ are represented herein as desktop computers, and compute device 25-2 is represented as a smartphone. However, it is to be understood that compute devices 25-1, 25-2, and 25-$n$ are not limited to the particular types of devices shown and that access to central controller 19 could alternatively be achieved by each reader 15 using other types of compute devices that are known in the art, such as tablet computers or kiosk-type compute workstations (e.g., for use by multiple readers 15 within a common facility). It is also to be understood that compute device 25 may be housed and/or function within (or be incorporated into) devices used for voice-recognition reporting, for an electronic medical record, for mammography reporting, for general radiology reporting, etc. As can be appreciated, in view of the above, compute devices 25-1 through 25-$n$ may be identical types of compute devices or may be different types of compute devices. Also, it is to be understood that, although each of compute devices 25-1, 25-2, and 25-$n$ is depicted as a single type of compute device, each of compute devices 25-1, 25-2, and 25-$n$ could comprise one or more compute devices used alternatively or in combination. In this manner, for example, reader 15-1 could, in some cases, for example, use a desktop to interface with central controller 19 and could, in other cases, use a smartphone or laptop to interface with central controller 19.

As noted above, each supervisor 17 represents any individual or entity that has any type of oversight authority (e.g., medical, administrative, financial, etc.) for screening mammograms read by one or more designated readers 15. Supervisors 17-1 through 17-$n$ are represented herein as being independently linked with central controller 19 using corresponding compute devices 27-1 through 27-$n$, respectively. Supervisors 17-1 through 17-$n$ may have access to the records or data of distinct groups of one or more readers 15 or may have access to the records or data of overlapping groups of one or more readers 15.

Compute device 27 represents any type of compute device that is adapted to interface with central controller 19 (e.g., through a designated web page or mobile application). Solely for purposes of example, compute devices 27-1 and 27-$n$ are represented herein as a desktop computer, and compute device 27-2 is represented herein as a smartphone. In a similar fashion to compute device 25, it is to be understood that access to central controller 19 could be achieved by each supervisor 17 using other types of compute devices that are known in the art, such as tablet computers or kiosk-type compute workstations. It is also to be understood that compute device 27 may be housed and/or function within (or be incorporated into) devices used for voice-recognition reporting, for an electronic medical record, for mammography reporting, for general radiology reporting, etc. As can be appreciated, in view of the above, compute devices 27-1 through 27-*n* may be identical types of compute devices or may be different types of compute devices. Also, it is to be understood that, although each of compute devices 27-1, 27-2, and 27-*n* is depicted as a single type of compute device, each of compute devices 27-1, 27-2, and 27-*n* could comprise two or more compute devices used alternatively or in combination. In this manner, for example, supervisor 17-1 could, in some cases, use a desktop to interface with central controller 19 and could, in other cases, use a smartphone or laptop to interface with central controller 19.

Method of Evaluating the Performance of Readers Using System 11

As referenced above, system 11 provides reader evaluation capabilities to interested managing parties. More specifically, system 11 provides reader evaluation capabilities through the use of three independent operations: (i) the aggregation of call-back request information for each reader 15 by performance evaluator 13, (ii) the analysis of call-back request information for one or more readers 15 by performance evaluator 13 based on one or more evaluative tools to yield a performance assessment of the reader 15 (i.e., relating to the proficiency of the reader in reading screening mammograms), and (iii) the reporting of reader performance by evaluator 13 to verified supervisors 17.

Aggregation of Reader Call-Back Request Information

Figure 2:
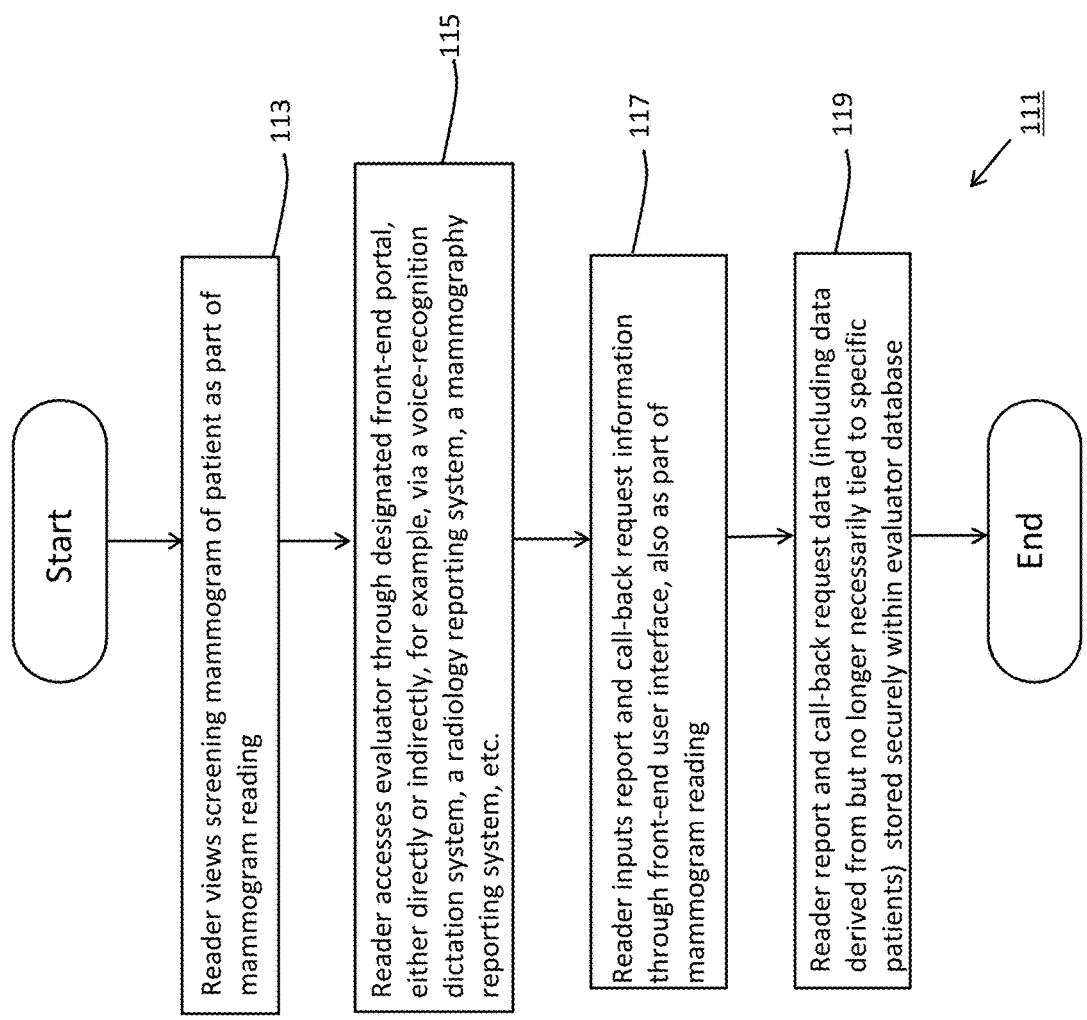
FIG. 2 is a flowchart depicting a method by which a screening mammogram reader may upload a screening mammogram report, including call-back request information, into the performance evaluator shown in FIG. 1.

Referring now to FIG. 2, there is shown a flowchart depicting an illustrative method for the aggregation of reader call-back request information by performance evaluator 13, the method being identified generally by reference numeral 111. As will be explained in detail below, call-back request information is input by each reader 15 by directly interfacing with central controller 19 through a designated software application. It is to be understood that the software application may be housed and/or function within (or be incorporated into) software applications used for voice-recognition reporting, for an electronic medical record, for mammography reporting, for general radiology reporting, etc.

Specifically, as a step 113 in method 111, a reader 15 views a screening mammogram of a patient as part of a mammogram reading. The screening mammogram of the patient may be obtained by the reader, himself or herself, or by a mammography technologist or other party. In some embodiments, the screening mammogram may be accessed electronically via a designated software application for mammography reporting. As part of step 113, reader 15 determines whether or not a call-back is required (i.e., whether additional testing is needed). If a call-back is required, reader 15 identifies the breast(s) in need of further examination (i.e., left breast, right breast, or both breasts).

Subsequent to or concurrent with step 113, reader 15 preferably directly interfaces with central controller 19 using an appropriate compute device 25, this interfacing step being identified as step 115 in FIG. 2. Preferably, for security purposes, each reader 15 is initially required to enter a username and password through a designated login page. In this manner, any data input by reader 15 is verified as valid. (Where the screening mammogram is accessed through a designated software application for mammography reporting, some or all of step 115 may be performed prior to step 113.) Additionally, it should be noted that, through a preliminary account creation process, it can be determined which supervisors 17 are authorized to access information for which readers 15. It should be noted that compute device 25, central controller 19, database 21, compute device 27, or any combination thereof, may be incorporated into one or more devices.

Once logged into central controller 19, reader 15 inputs a report, including certain call-back request-related information, through a front-end user interface (UI) in step 117. Thereafter, the user-confirmed information is uploaded onto central controller 19 and, in turn, is securely stored in database 21 as part of data transmission step 119.

Figure 3:
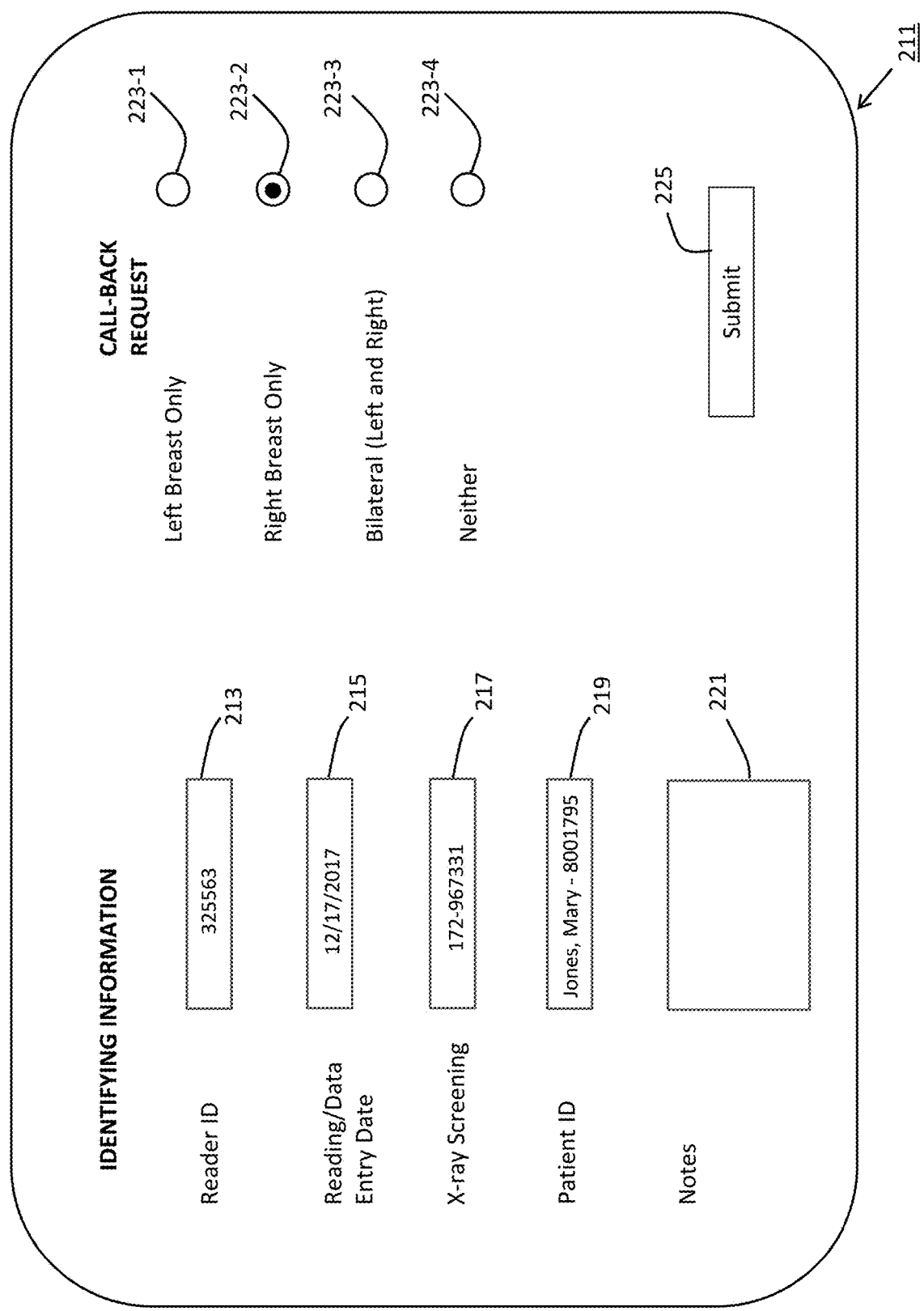
FIG. 3 is a sample screen display of a user interface designed for a screening mammogram reader for uploading a report, including call-back request information, into the performance evaluator shown in FIG. 1.

Referring now to FIG. 3, there is shown a sample screen display of the front-end UI utilized by reader 15 to input the report, including call-back request-related data, in step 117, the screen display being identified generally by reference numeral 211. As can be seen, screen display 211 is designed to request both identifying information for a particular screening, as well as the call-back request determination.

Namely, with respect to the identifying information, reader 15 is prompted to input (i) a unique identifier associated with the reader via a radiologist ID window 213, the unique identifier preferably self-propagating within window 213 using the previously-received user login data, (ii) a reading date (i.e., the date the screening mammogram is read and the data is entered into the system) via reading/data entry date window 215, (iii) an x-ray screening identifier (i.e., means for uniquely identifying the x-ray session) via an x-ray screening window 217, and (iv) a patient identifier (e.g., a patient name and/or number) via patient ID window 219. Additionally, a notes window 221 is provided to enable reader 15 to input any miscellaneous information that he/she considers notable. If desired, the notes window 221 could be used to contain the substance of what has historically been the report for the reading. Although not shown, screen display 211 could be configured to permit the uploading of the screening mammograms read by the reader 15.

Screen display 211 additionally includes means for selecting one of the four possible call-back request options. In the present embodiment, the four possible call-back request options, namely, left breast, right breast, bilateral, and neither, are represented through the use of corresponding radio buttons 223-1 through 223-4, respectively. However, it is to be understood that alternative types of UI designs (e.g., a dropdown window or checkboxes) could be used in place thereof without departing from the spirit of the present invention.

With all pertinent identifying and call-back request information thus inputted into screen display 211, reader 15 then submits the data through actuation of a corresponding button 225. As will be explained further below, the aggregated data is stored by performance evaluator 19 with other readings inputted by the same reader and by different readers and may be analyzed as a comprehensive collection to evaluate reader performance.

It is to be understood that the front end UI exemplified by screen display 211 could be incorporated into a designated software application for mammography reporting. In such an embodiment, screen display 211 could be modified so that the patient identifying information (i.e., the information in one or more of windows 213, 215, 217 and 219) is omitted entirely therefrom. In addition, in such an embodiment, a reader may access a patient's screening mammograms (for example, by clicking on a patient's name or other identifier) and may also gain access to screen display 211 or some variation thereof.

Also, it is to be understood that, instead of having the reader actively make a selection of a call-back request option, such as by clicking on one of radio buttons 223-1 through 223-4, system 11 could be configured to automatically extract from the reader's report the information as to whether a call-back request is to be issued to a patient with respect to a left breast, a right breast, both breasts, or not at all.

Analysis of Call-back Information by Performance Evaluator 13

As noted above, central controller 19 engages in arithmetic and/or statistical analysis of call-back request metrics accumulated for each radiologist 15 to assess performance efficacy. More specifically, central controller 19 evaluates historical call-back request metrics for each reader 15 to determine, inter alia, (i) unacceptable deviations in unilateral call-back requests relative to a defined threshold and (ii) unacceptable deviations in bilateral call-back requests relative to a defined threshold.

Referring now to FIG. 4, there is shown an illustrative chart that is useful in understanding the process by which central controller 19 evaluates unilateral call-back request data to assess reader performance, the chart being represented generally by reference numeral 311. As can be seen, chart 311 includes (i) a reader column 313, which lists all readers 15-1 through 15-n assessed by performance evaluator 13, (ii) a total unilateral call-back request column 315, which lists the total number of unilateral call-back requests (i.e., the sum of left and right call-back requests) issued by each reader 15, (iii) a left breast call-back request column 317, which lists the total number of left breast call-back requests that are issued by each reader 15, as well as the corresponding percentage (indicated in parentheses) of total call-back requests for each reader 15 represented by said total number of left breast call-back requests, (iv) a right breast call-back request column 319, which lists the total number of right breast call-back requests that are issued by each reader 15, as well as the corresponding percentage (indicated in parentheses) of total call-back requests for each reader 15 represented by said total number of right breast call-back requests, and (v) a statistical conclusion column 321, which provides an assessment of unilateral call-back request performance for each reader 15 based on the values provided in columns 315, 317 and 319 according to the evaluative method discussed below. Although chart 311 shows results for three readers, namely, readers 15-1, 15-2, and 15-n, it is to be understood that chart 311 could include results for a greater number of readers 15 or could include results for a lesser number of readers 15. It is also to be understood that analysis may be performed with regard to a particular radiologist, a particular group of radiologists, other types of readers, and/or over a particular time period.

It is well-known that left-sided breast cancer occurs with very slightly greater frequency than right-sided breast cancer in some areas of the world. In the U.S., the ratio of incidences of left-sided breast cancer to right-sided breast cancer is most often reported as, and believed by the present inventor to be, about 50/50 (for example, approximately 51% to 49%). Although the cause for the reportedly slightly greater incidence of left-sided breast cancer in the U.S. (or a slightly greater incidence of right-sided breast cancer in those countries experiencing an opposite disparity) is not known, the above-noted left/right disparity is not believed to be due to any perceptual partiality on the part of readers. (See, for example, Tan et al., "Comparison of readers' detection of right-sided and left-sided breast cancers and microcalcifications," Journal of Medical Imaging and Radiation Oncology, 55:353-361 (2011), which is incorporated herein by reference.) In fact, to the contrary, the literature is completely silent about the possibility that some readers may demonstrate a lateral bias toward one breast or the other. Nonetheless, the present inventor believes that such bias is not merely a theoretical concern, and may be due to a number of causes; for instance, whether the reader preferentially reads right breasts or left breasts first, whether the reader has a visual field defect, how or where the images are arranged on the computer monitor(s) used to view the mammogram images with respect to the position of the radiologist when viewing, the hanging protocol (the sequence in which each of the current and prior images are displayed, and where on the viewing monitor(s) they are placed for viewing during that sequence), whether the reader has a subconscious laterality bias on a basis other than visual field defect, and, if viewed by two readers jointly (which often happens at academic sites), whether the reader with ultimate authority over the final version of the reading is seated during viewing to the right or to the left of the other viewer.

With this in mind, the present invention is predicated, at least in part, on the discovery by the present inventor that such bias can be detected and measured; that the relative numbers of left breast call-back requests to right breast call-back requests for a reader may be used to determine the presence or absence of a lateral (i.e., left or right) bias by the reader. Such a bias represents a quality concern, raising the questions of whether the radiologist(s) is(are) engendering too many call-back requests on one side or too few on the other. Without first detecting such bias, one cannot aim to improve quality by rectifying the bias.

To this end, central controller 19 may assess the performance of a reader (or readers) by comparing the observed numbers of left and right call-back requests to expected numbers of left and right call-back requests based on the number of unilateral call-back requests reported in mammogram readings and the established rates of incidence of left and right breast cancers for the subject population (e.g., approximately 51% left breast cancer rate and approximately 49% right breast cancer rate in the U.S.). Such a comparison typically takes into account (1) the differential between the observed unilateral call-back request ratio and the expected unilateral call-back request ratio and (2) the sample size. More specifically, such a comparison may involve using any one or more of a number known statistical tests, such as a chi-square test, to determine whether the difference between the observed call-back request numbers and the expected call-back request numbers, based on the sample size, falls within an acceptable range of performance (i.e., may be considered insignificant or simply due to random variation). The approach described above can, therefore, be applied to chart 311 to generate performance conclusions to be incorporated into column 321.

For instance, in the example shown in FIG. 4, reader 15-1 has issued 60 unilateral call-back requests and, for these 60 unilateral call-back requests, has issued 32 left breast call-back requests, for a left breast call-back request percentage of 53.3%, and 28 right breast call-back requests, for a right breast call-back request percentage of 46.7%. Using, for example, a chi-square test ($x_c^2 = \Sigma[(f_o-f_c)^2/f_c]$ wherein $f_o$ is the observed number of left (or right) call-back requests, c is the degrees of freedom, and $f_c$ is the expected number of left (or right) call-back requests), one can compare these results to expected numbers of 30 left breast call-back requests (corresponding to approximately 50% of 60 call-back requests) and 30 right breast call-back requests (corresponding to approximately 50% of 60 call-back requests). Using a significance level of p<0.05, these results would yield a chi-square statistic of 0.1335 and p-value of 0.715, which would be regarded as falling within a range of acceptable performance (or the difference from expected regarded as insignificant or random). Thus, an indication of "acceptable performance" would be indicated in statistical conclusion column 321 of chart 311 for reader 15-1. By comparison, reader 15-2 has issued 75 unilateral call-back requests and, for these 75 unilateral call-back requests, has issued 50 left breast call-back requests, for a left breast call-back request percentage of 66.7%, and 25 right breast call-back requests, for a right breast call-back request percentage of 33.3%. Comparing these results to expected values of 38 left breast call-back requests (corresponding to approximately 50% of 75 call-back requests) and 37 right breast call-back requests (corresponding to approximately 50% of 75 call-back requests) and using the above-described chi-square test and a significance level of p<0.05, these results would yield a chi-square statistic of 3.959 and a p-value of 0.047, which would be regarded as falling outside a range of acceptable performance (i.e., the difference from expected regarded as significant or likely not simply random). Thus, an indication of "unacceptable performance" would be indicated in statistical conclusion column 321 of chart 311 for reader 15-2. In addition, an indication as to why the performance is regarded as unacceptable may also be provided in column 321. For example, as in FIG. 4, an indication may be provided that the left/right ratio is too high. Lastly, reader 15-n has issued 4 unilateral call-back requests and, for these 4 unilateral call-back requests, has issued 3 left breast call-back requests, for a left breast call-back request percentage of 75%, and 1 right breast call-back request, for a right breast call-back request percentage of 25%. Comparing these results to expected values of 2 left breast call-back requests (corresponding to approximately 51% of 4 call-back requests) and 2 right breast call-back requests (corresponding to approximately 49% of 4 call-back requests) and using the above-described chi-square test and a significance level of p<0.05, these results would be regarded as falling within a range of acceptable performance (p=0.465). Thus, an indication of "acceptable performance" would be indicated in statistical conclusion column 321 of chart 311 for reader 15-n. As can be appreciated, although the type of statistical test used in the present example is a chi-square test with a p-value of 0.05, one could vary the p-value and/or use other statistical tests.

The present invention is also predicated, at least in part, on the discovery that a reader's bilateral call-back request rate may signal the presence or absence of a pro/anti bilateral call-back request bias by the reader. To this end, central controller 19 may assess the performance of a reader (or one or more readers) by comparing the observed number of bilateral call-back requests to an expected number of bilateral call-back requests and indicating whether or not the observed bilateral call-back request rate falls within an acceptable range of performance. Such a comparison preferably takes into account (1) the differential between the observed bilateral call-back request rate and an expected bilateral call-back request rate and (2) the sample size.

As noted above, the sample size denominators in the rate calculations of observed versus expected rates may be either all screening mammograms or all call-back requests. Such a comparison may involve using known statistical tests, such as a chi-square test. Because specifically bilateral call-back request rate has not been investigated previously as a metric of reader performance, there is not, at present, an established norm or preferred value for bilateral call-back request rate. Nevertheless, based on his decades of experience in clinical mammography as a diagnostic radiologist and teacher of mammography to radiologists in training, the present inventor believes that the following examples are illustrative of realistic acceptable upper and lower limits for evaluating a bilateral call-back request rate of a reader (or reader(s)): (1) where the bilateral call-back request rate is based on a percentage of all screening mammograms, an upper limit of 4% bilateral call-back requests and a lower limit of 0% bilateral call-back requests; and (2) where the bilateral call-back request rate is based on a percentage of all call-back requests (i.e., the sum of unilateral call-back requests and bilateral call-back requests), an upper limit of 20% bilateral call-back requests and a lower limit of 1% bilateral call-back requests.

Referring now to FIG. 5, there is shown an illustrative chart that is useful in understanding the process by which central controller 19 evaluates bilateral call-back request data to assess reader performance, the chart being represented generally by reference numeral 411. As can be seen, chart 411 includes (i) a reader column 413, which lists all readers 15-1 through 15-n assessed by performance evaluator 13, (ii) a total screenings column 415, which lists the total number of screenings performed by each reader 15, (iii) a bilateral call-back request column 417, which lists the total number of bilateral call-back requests, as well as the corresponding percentage (indicated in parentheses) of bilateral call-back requests relative to the total number of screenings for each reader 15, and (iv) a conclusion column 419, which provides an assessment of bilateral call-back request performance for each reader 15 based on the values provided in columns 415 and 417 according to the evaluative method employed. Although chart 411 shows results for three readers, namely, readers 15-1, 15-2, and 15-n, it is to be understood that chart 411 could include results for a greater number of readers 15 or could include results for a lesser number of readers 15.

With this in mind, for instance, reader 15-1 has conducted 728 screenings and has issued 44 bilateral call-back requests, representing a bilateral call-back request rate of 6.0%. Performance could, for example, be assessed in at least two ways: using a simple arithmetic comparative (or non-statistical) approach in which the bilateral recall request rate is simply compared to the upper limit of acceptable (e.g., 4%), or using a chi-square test or other statistical method with 4% (for example) of the total number of screenings used as the expected frequency of bilateral call-back requests. In the former way (i.e., simple arithmetic comparison), one would simply determine if the bilateral request rate exceeds the upper limit of 4%. Proceeding in this fashion, since the bilateral request rate in this case is 6.0%, which is greater than 4%, one would say that this reader has a bilateral request rate outside that considered acceptable. However, in the latter way (i.e., employing a chi-square test or other statistical method), one can compare the observed numbers of 44 bilateral call-back requests and 684 other outcomes (i.e., unilateral call-back requests and no call-back requests) to expected numbers of 29 bilateral call-back requests (corresponding to approximately 4% of 728 call-back requests) and 699 others. Using a significance of p<0.05 for the chi-square statistic, these results would be regarded as falling within a range of acceptable performance (p=0.07). Thus, an indication of "acceptable performance" would be indicated in conclusion column 419 of chart 411 for reader 15-1. (On the other hand, had the upper limit assessment of the simple arithmetic comparison been employed, the performance evaluation provided in column 419 of chart 411 for reader 15-1 would have been "unacceptable.")

By comparison, reader 15-2 has conducted 911 screenings and has issued 1 bilateral call-back request, representing a bilateral call-back ratio of 0.1%. Using a chi-square test and comparing the observed numbers of 1 bilateral call-back and 910 other outcomes to expected values of 36 bilateral call-backs (based on an upper limit of 4% of 911 call-backs) and 875 other outcomes and using a significance of p<0.05, these results would be regarded as falling outside a range of acceptable performance (p<0.00001). Thus, an indication of "unacceptable performance" would be indicated in conclusion column 419 of chart 411 for reader 15-2. If, however, the simple arithmetic comparative approach had been employed, then performance would have been judged as "acceptable" since the bilateral recall request rate falls within the range defined by the lower limit of 0% and the upper limit of 4%.

In addition, where the performance is determined to be unacceptable, an indication as to why the performance is regarded as unacceptable may also be provided in column 419. For example, as in FIG. 5, an indication may be provided that the bilateral recall request rate is too low. Thus, an indication of "unacceptable performance" would be indicated in conclusion column 419 of chart 411 for reader 15-2.

Lastly, reader 15-$n$ has conducted 25 screenings and has issued 2 bilateral call-back requests, representing a bilateral call-back request rate of 8.0%. Comparing the observed numbers of 2 bilateral call-back requests and 23 other outcomes to expected values of 1 bilateral call-back request (corresponding to approximately 4% of 25 call-back requests) and 24 other outcomes (corresponding to approximately 96% of 25 call-back requests) and using the above-described chi-square test and a significance of p<0.05, these results would be regarded as falling within a range of acceptable performance (p=0.55). Thus, an indication of "acceptable performance" would be indicated in conclusion column 419 of chart 411 for reader 15-$n$. As can be appreciated, although the type of statistical test used in the present example is a chi-square test with a p-value of 0.05, one could vary the p-value and/or use other statistical tests. Or, one could use a simple arithmetic (non-statistical) test, such as simple comparison to an accepted upper limit. So, had 4% been chosen as the value for upper limit of acceptable, then, in this instance (i.e., 8%), the bilateral call-back request rate would be considered "unacceptable performance."

It should be understood that, although chart 411 is predicated on a methodology in which the bilateral call-back request rate is based on the total number of screenings performed, one could employ a methodology in which the bilateral call-back request rate is based on the total number of call-back requests issued.

Other evaluative metrics, including conventional evaluative metrics, using the call-back request data input by reader 15 with screen display 211 could additionally be performed by central controller 19 to further evaluate reader performance without departing from the spirit of the present invention. For instance, overall call-back request frequency (the sum of unilateral and bilateral call-back requests) relative to total screenings could additionally be compiled and evaluated to determine reader performance. Moreover, screen display 211 could be modified to also include fields for inputting other information used in conventional evaluative metrics.

Reader Performance Review by Supervising Entities 17

Figure 6:
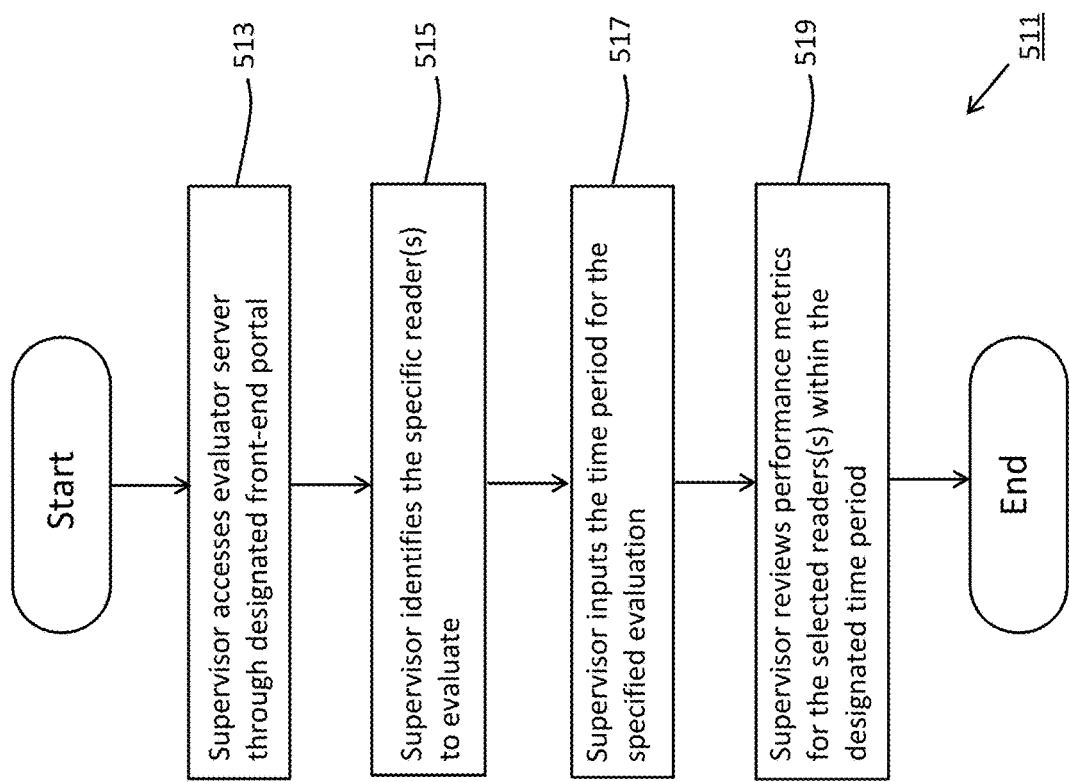
FIG. 6 is a flowchart depicting a method by which another individual, such as a medical supervisor or administrator, may access information from the performance evaluator shown in FIG. 1 in order to ascertain the performance of one or more screening mammogram readers.

As referenced above, supervisors 17 can access relevant call-back request information for either an individual reader 15 or a group of related readers 15 (e.g., a team of radiologists operating out of a common hospital). Referring now to FIG. 6, there is shown a flowchart depicting an illustrative method for reviewing call-back request information by a supervising entity 17 in order to assess reader performance, the method being identified generally by reference numeral 511.

In order to review reader performance, a supervisor 17 directly interfaces with central controller 19 using an appropriate compute device 25, this interfacing step being identified as step 513 in FIG. 6. Preferably, for security purposes, each supervisor 17 is initially required to enter a username and password through a designated login page. In this manner, by cross-referencing supervisor access against an authorization table stored in database 21, supervisor 17 can be restricted access to call-back request information for only those readers 15 who are verified as being under his/her supervision.

Once logged into central controller 19, supervisor 17 utilizes a front-end user interface (UI) to identify the specific set of readers 15 to evaluate, this reader identification step being represented as step 515 in FIG. 6. Additionally, in step 517, the supervisor 17 restricts the review to a desired time period in which screening mammograms were performed. Once the aforementioned information is properly submitted by supervisor 17, central controller 19 displays the requested performance results within a designated panel on the supervisor UI. Accordingly, in step 519, a supervisor 17 can then review information relating to the requested reader performance.

Figure 7:
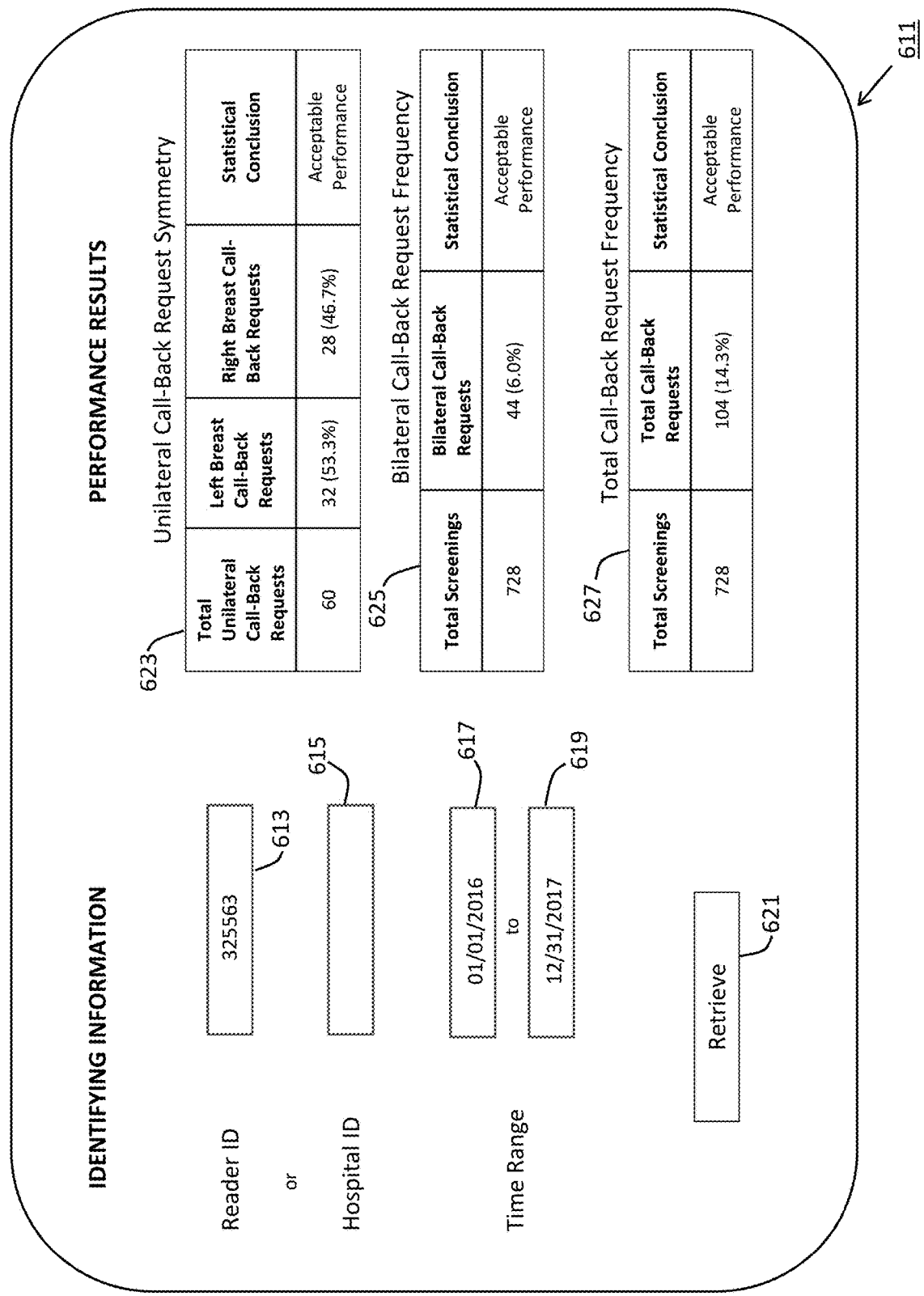
FIG. 7 is a sample screen display of a user interface for a supervisor, administrator or other individual to access information from the performance evaluator about the performance of one or more screening mammogram readers.

Referring now to FIG. 7, there is shown a sample screen display of the front-end UI utilized by supervisor 17 to both (i) input the information required in steps 515 and 517, and (ii) display the retrieved reader performance results in step 519, the screen display being identified generally by reference numeral 611. As can be seen, screen display 611 separates the identifying information, which specifies the reader(s) and time frame for the requested assessment, from the retrieved assessment results into two distinct regions, or panels, within the same user interface.

As part of the identifying information panel of the supervisor UI, screen display 611 prompts supervisor 17 to input the specific reader(s) to be evaluated. Specifically, supervisor 17 can either input (i) a unique identifier associated with a single reader via a reader ID window 613, or (ii) a unique identifier associated with a designated group of readers (e.g. readers from a common hospital) via a hospital ID window 615.

Additionally, the identifying information panel of the supervisor UI prompts supervisor 17 to input the time range for the requested assessment. Specifically, screen display 611 prompts supervisor 17 to input both (i) the start date of the requested time period via start date window 617 and (ii) the end date of the requested time period via end date window 619. With all pertinent identifying information input via windows 613, 615, 617 and 619, supervisor 17 sends a results retrieval request through actuation of a corresponding button 621.

In response to the retrieval request, the performance results panel of the supervisor UI displays the requested information in a highly intuitive fashion for review by supervisor 17. Specifically, as shown herein, the performance results panel of the supervisor UI comprises (i) a unilateral call-back request symmetry chart 623, which displays not only aggregated unilateral call-back request data for the identified reader(s) during the specified time period but also a statistical conclusion (i.e. an overall performance assessment) calculated using such data, (ii) a bilateral call-back request chart 625, which displays not only aggregated bilateral call-back request data for the identified reader(s) during the specified time period but also a statistical conclusion (i.e. an overall performance assessment) calculated using such data, and (iii) a total call-back request frequency chart 627, which displays not only aggregated call-back request data for the identified reader(s) during the specified time period but also a statistical conclusion (i.e. an overall performance assessment) calculated using such data. Where the statistical conclusion for any of charts 623, 625, and 627 indicates that performance is unacceptable, such a conclusion may be accompanied by an explanation (e.g., left/right call-back request ratio is too high or too low, bilateral call-back request rate is too high or too low, call-back request frequency is too high or too low, etc.).

As can be appreciated, system 11 may be configured so that not only may a supervisor access the performance results of one or more readers after actuating the retrieve button 621 but also may automatically receive a notification from performance evaluator 13, for example, to the supervisor's compute device whenever the performance of one or more readers goes outside of an acceptable range for one or more of the analyzed metrics. For example, such a notification may convey the identity of the one or more readers whose performance is outside of an acceptable range, the metric in question (e.g., unilateral call-back request symmetry, bilateral request frequency, etc.), and an explanation of how the performance is unacceptable (i.e., too high or too low).

As discussed above, system 11 is configured so that the performance results for one or more readers 15 can be accessed by an authorized supervisor 17. However, if desired, such performance results may additionally be made accessible to the readers, themselves, so that each reader may view his/her own performance results.

The embodiments of the present invention described above are intended to be merely exemplary and those skilled in the art shall be able to make numerous variations and modifications to them without departing from the spirit of the present invention. All such variations and modifications are intended to be within the scope of the present invention as defined in the appended claims.

What is claimed is:

1. A system for electronically evaluating the performance of at least one screening mammogram reader in reading at least one screening mammogram, each of the at least one screening mammogram comprising an image of a left breast of a patient and an image of a right breast of the patient arranged in a correct left-right orientation, the system comprising:

a first compute device, the first compute device comprising a first screening mammogram reader user interface designed for use by a first screening mammogram reader to electronically input call-back request information, wherein the call-back request information comprises an indication as to whether, for each screening mammogram read by the first screening mammogram reader, a unilateral call-back request if advised, is for the left breast of the patient or for the right breast of the patient;

a performance evaluator, the performance evaluator comprising a central controller and a data storage device, wherein the central controller and the data storage device are in electronic communication with one another, wherein the central controller of the performance evaluator is in electronic communication with the first compute device to enable the call-back request information for unilateral call-back requests for the first screening mammogram reader to be uploaded from the first compute device to the central controller for aggregation, wherein the central controller for the performance evaluator is configured to make an assessment of whether or not lateral bias exists for the first screening mammogram reader based on the aggregated unilateral call-back request information, the central controller being configured to make the assessment of lateral bias by comparing observed numbers of left and right call-back requests to expected numbers of left and right call-back requests for an aggregate number of screening mammograms read by the first screening mammogram reader, and wherein the data storage device is configured to retrievably store the assessment of lateral bias for the first screening mammogram reader; and a second compute device, the second compute device comprising a supervising entity user interface designed for use by a first supervising entity, wherein the second compute device is in electronic communication with the central controller, and wherein the second compute device is configured to electronically receive the assessment of lateral bias for the first screening mammogram reader from the central controller and to display the assessment on the supervising entity user interface.

2. The system as claimed in claim 1 wherein the central controller compares the observed numbers of left and right breast call-back requests for the first screening mammogram reader to expected numbers of left and right breast call-back requests, respectively, using a chi-square test, other statistical evaluation and/or simple arithmetic comparison.

3. The system as claimed in claim 1 wherein the first compute device is selected from the group consisting of one or more of a desktop computer, a laptop computer, a smartphone, and a kiosk-type workstation, whether used alternatively or in combination.

4. The system as claimed in claim 1 wherein the second compute device is selected from the group consisting of one or more of a desktop computer, a laptop computer, a smartphone, and a kiosk-type workstation, whether used alternatively or in combination.

5. The system as claimed in claim 1 wherein the performance evaluator automatically sends a notification to the second compute device in the event that the central controller determines a presence of lateral bias.

6. The system as claimed in claim 1 further comprising a third compute device, the third compute device comprising a second screening mammogram reader user interface designed for use by a second screening mammogram reader to electronically input call-back request information, wherein the call-back request information comprises an indication as to whether a unilateral call-back request, if advised, is for a left breast or for a right breast, the third compute device being in electronic communication with the central controller, to enable the call-back request information for unilateral call-back requests associated with the second screening mammogram reader to be uploaded from the third compute device to the central controller, the central controller for the performance evaluator being configured to make an assessment of whether or not lateral bias exists for the second screening mammogram reader based on the aggregated unilateral call-back request information, and wherein the second compute device is configured to electronically receive the assessment of lateral bias associated with the second screening mammogram reader from the central controller and to display the assessment on the supervising entity user interface.

7. The system as claimed in claim 6 wherein the assessment of lateral bias for the second screening mammogram reader is retrievable by the first supervising entity using the second compute device.

8. The system as claimed in claim 1 wherein at least one of the performance evaluator and the first compute device is integrated with at least one of voice-recognition software and/or hardware; an electronic medical record apparatus; mammography reporting and analysis software; and radiology reporting software and/or hardware.

9. A system for electronically evaluating the performance of at least one screening mammogram reader, the system comprising:
   a first compute device, the first compute device comprising a first screening mammogram reader user interface designed for use by a first screening mammogram reader to electronically input call-back request information, wherein the call-back request information comprises an indication as to whether or not the first screening mammogram reader is advising a bilateral call-back request;
   a performance evaluator, the performance evaluator comprising a central controller and a data storage device, wherein the central controller and the data storage device are in electronic communication with one another, wherein the central controller of the performance evaluator is in electronic communication with the first compute device to enable the call-back request information associated with the first screening mammogram reader to be uploaded from the first compute device to the central controller for aggregation, wherein the central controller for the performance evaluator is configured to make an assessment of whether or not bilateral bias exists for the first screening mammogram reader using the aggregated call-back request information, the central controller being configured to make the assessment of bilateral bias by comparing an observed number of bilateral call-back requests for the first screening mammogram reader to an expected number of bilateral call-back requests for the first screening mammogram reader, and wherein the data storage device is configured to retrievably store the assessment of bilateral bias for the first screening mammogram reader; and
   a second compute device, the second compute device comprising a supervising entity user interface designed for use by a first supervising entity, wherein the second compute device is in electronic communication with the central controller, and wherein the second compute device is configured to electronically receive the assessment of bilateral bias for the first screening mammogram reader from the central controller and to display the assessment on the supervising entity user interface.

10. The system as claimed in claim 9 wherein the aggregated call-back request information comprises an observed number of bilateral call-back requests and an observed number of other outcomes for the first screening mammogram reader and wherein the central controller assesses bilateral bias by comparing the observed numbers of bilateral call-back requests and other outcomes for the first screening mammogram reader to expected numbers of bilateral call-back requests and other outcomes, respectively.

11. The system as claimed in claim 10 wherein the central controller compares the observed numbers of bilateral call-back requests and other outcomes for the first screening mammogram reader to expected numbers of bilateral call-back requests and other outcomes, respectively, using a chi-square test, other statistical evaluation and/or simple arithmetic comparison.

12. The system as claimed in claim 9 wherein the first compute device is selected from the group consisting of one or more of a desktop computer, a laptop computer, a smartphone, and a kiosk-type workstation, whether used alternatively or in combination.

13. The system as claimed in claim 9 wherein the second compute device is selected from the group consisting of one or more of a desktop computer, a laptop computer, a smartphone, and a kiosk-type workstation, whether used alternatively or in combination.

14. The system as claimed in claim 9 further comprising a third compute device, the third compute device comprising a second screening mammogram reader user interface designed for use by a second screening mammogram reader to electronically input call-back request information, wherein the call-back request information comprises an indication as to whether or not the second screening mammogram reader is advising a bilateral call-back request, the third compute device being in electronic communication with the central controller to enable the call-back request information for bilateral call-back requests associated with the second screening mammogram reader to be uploaded from the third compute device to the central controller, the central controller for the performance evaluator being configured to make an assessment of whether or not bilateral bias exists for the second screening mammogram reader based on the aggregated bilateral call-back request information.

15. The system as claimed in claim 14 wherein the assessment of bilateral bias for the second screening mammogram reader is retrievable by the first supervising entity using the second compute device.

16. The system as claimed in claim 9 wherein at least one of the performance evaluator and the first compute device is integrated with at least one of voice-recognition software and/or hardware; an electronic medical record apparatus; mammography reporting and analysis software; and radiology reporting software and/or hardware.

17. The system as claimed in claim 9 wherein the central controller is configured to assess bilateral bias based on the observed number of bilateral call-back requests compared to the expected number of bilateral call-back requests for all screening mammograms read by the first screening mammogram reader over a given period of time.

18. The system as claimed in claim 9 wherein the central controller is configured to assess bilateral bias based on the observed number of bilateral call-back requests compared to the expected number of bilateral call-back requests for all call-back requests made by the first screening mammogram reader over a given period of time.

19. A system for electronically evaluating the performance of at least one screening mammogram reader, the system comprising:
   a first compute device, the first compute device comprising a first screening mammogram reader user interface designed for use by a first screening mammogram reader to electronically input call-back request information, wherein the call-back request information comprises an indication that a call-back is being advised for one of four options selected from a left breast, a right breast, both breasts, and neither breast;
   a performance evaluator, the performance evaluator comprising a central controller and a data storage device, wherein the central controller and the data storage device are in electronic communication with one another, wherein the central controller of the performance evaluator is in electronic communication with the first compute device to enable the call-back request information associated with the first screening mammogram reader to be uploaded from the first compute device to the central controller for aggregation, wherein the central controller for the performance evaluator, is configured to operate in at least three alternative modes, wherein a first alternative mode of the at least three alternative modes comprises making an assessment of whether or not lateral bias exists for unilateral call-back requests for the first screening mammogram reader by comparing observed numbers of left and right call-back requests for the first screening mammogram reader to expected numbers of left and right call-back requests for the first screening mammogram reader, wherein a second alternative mode of the at least three alternative modes comprises making an assessment of whether or not bilateral bias exists for the first screening mammogram reader by comparing an observed number of bilateral call-back requests for the first screening mammogram reader to an expected number of bilateral call-back requests for the first screening mammogram reader, and wherein a third alternative mode of the at least three alternative modes comprises making the assessment of lateral bias of the first alternative mode and making the assessment of bilateral bias of the second alternative mode, and wherein the data storage device is configured to retrievably store the assessment of lateral bias of the first screening mammogram reader and/or the assessment of bilateral bias of the first screening mammogram reader; and
   a second compute device, the second compute device comprising a supervising entity user interface designed for use by a first supervising entity, wherein the second compute device is in electronic communication with the central controller, and wherein the second compute device is configured to electronically receive from the central controller the assessment of lateral bias for the first screening mammogram reader and/or the assessment of bilateral bias for the first screening mammogram reader and to display the assessment of lateral bias and/or the assessment of bilateral bias on the supervising entity user interface.

20. The system as claimed in claim 19 wherein at least one of the performance evaluator and the first compute device is integrated with at least one of voice-recognition software and/or hardware; an electronic medical record apparatus; mammography reporting and analysis software; and radiology reporting software and/or hardware.

21. A system for electronically evaluating the performance of one or more screening mammogram readers, the system comprising:
   a first set of one or more compute devices, each of the first set of one or more compute devices comprising a screening mammogram reader user interface designed for use by at least one screening mammogram reader to electronically input call-back request information, wherein the call-back request information comprises an indication that a call-back is being advised for one of four options selected from a left breast, a right breast, both breasts, and neither breast;
   a performance evaluator, the performance evaluator comprising a central controller and a data storage device, wherein the central controller and the data storage device are in electronic communication with one another, wherein the central controller of the performance evaluator is in electronic communication with each of the first set of one or more compute devices to enable the call-back request information associated with the one or more screening mammogram readers to be uploaded from the first set of one or more compute devices to the central controller for aggregation, wherein the central controller for the performance evaluator is configured to operate in at least three alternative modes, wherein a first alternative mode of the at least three alternative modes comprises making an assessment of whether or not lateral bias exists for unilateral call-back requests for the screening mammogram readers, assessed individually and/or collectively, by comparing observed numbers of left and right call-back requests for the screening mammogram readers to expected numbers of left and right call-back requests for the screening mammogram readers, individually and/or collectively, wherein a second alternative mode of the at least three alternative modes comprises making an assessment of whether or not bilateral bias exists for the screening mammogram readers, assessed individually and/or collectively, by comparing an observed number of bilateral call-back requests for the screening mammogram readers to an expected number of bilateral call-back requests for the screening mammogram readers, individually and/or collectively, and wherein a third alternative mode of the at least three alternative modes comprises making the assessment of lateral bias of the first alternative mode and making the assessment of bilateral bias of the second alternative mode, and wherein the data storage device is configured to retrievably store the assessment of lateral bias of the screening mammogram readers and/or the assessment of bilateral bias of the screening mammogram readers; and
   at least one second compute device, the at least one second compute device comprising a supervising entity user interface designed for use by a first supervising entity, wherein the second compute device is in electronic communication with the central controller, and wherein the second compute device is configured to electronically receive from the central controller the assessment of lateral bias for the screening mammogram readers and/or the assessment of bilateral bias for the screening mammogram readers and to display the assessment of lateral bias and/or the assessment of bilateral bias on the supervising entity user interface.

\* \* \* \* \*